(12) United States Patent
Chen et al.

(10) Patent No.: US 10,835,563 B2
(45) Date of Patent: Nov. 17, 2020

(54) METHOD FOR PREVENTING, POSTPONING OR TREATING CHANGES IN THE ANTERIOR/POSTERIOR CHAMBER VOLUME, VITREOUS HUMOUR, AND/OR RETINAL DETACHMENT

(71) Applicant: GRAPE KING BIO LTD., Taoyuan (TW)

(72) Inventors: Chin-Chu Chen, Taoyuan (TW); Shu-Hsing Yeh, Taoyuan (TW); Li-Ya Lee, Taoyuan (TW); Jui-Hsia Hsu, Taoyuan (TW)

(73) Assignee: GRAPE KING BIO LTD., Taoyuan (TW)

( * ) Notice: Subject to any disclaimer, the term of this patent is extended or adjusted under 35 U.S.C. 154(b) by 116 days.

(21) Appl. No.: 16/227,530

(22) Filed: Dec. 20, 2018

(65) Prior Publication Data
US 2020/0061134 A1  Feb. 27, 2020

(30) Foreign Application Priority Data
Aug. 24, 2018 (TW) .............................. 107129637 A

(51) Int. Cl.
| | | |
|---|---|---|
| *A61K 36/68* | (2006.01) | |
| *A61K 36/068* | (2006.01) | |
| *C12N 1/04* | (2006.01) | |
| *C12N 1/14* | (2006.01) | |
| *A23L 29/00* | (2016.01) | |
| *A61K 9/00* | (2006.01) | |

(52) U.S. Cl.
CPC .......... *A61K 36/068* (2013.01); *A23L 29/065* (2016.08); *A61K 9/0053* (2013.01); *C12N 1/04* (2013.01); *C12N 1/14* (2013.01); *A23V 2002/00* (2013.01); *A23V 2250/208* (2013.01)

(58) Field of Classification Search
None
See application file for complete search history.

(56) References Cited

U.S. PATENT DOCUMENTS

2016/0312176 A1  10/2016  Lin et al.

FOREIGN PATENT DOCUMENTS

| TW | 201816116 A | 5/2018 |
|---|---|---|
| TW | 201906623 A | 2/2019 |

OTHER PUBLICATIONS

Weng et al., Journal of Ethnopharmacology, vol. 83, pp. 79-85, 2002.*
Wang et al., Brazilian Journal of Microbiology, vol. 43, No. 2, pp. 449-455, 2012.*
Ng et al., Journal of Pharmacy and Pharmacology, vol. 57, pp. 1509-1519, 2005.*
Yue et al., Journal of Pharmacy and Pharmacology, vol. 65, No. 4, pp. 474-493, 2013.*
Tuli et al., 3 Biotech, vol. 4, No. 1, pp. 1-12, 2014.*
Hsu et al., "Healthcare Functions of Cordyceps cicadae", J Nutr Food Sci, 2015, vol. 5, Issue 6, total 7 pages.
Lin et al., "Fermented Cordyceps cicadae Mycelia Extracts Ameliorate Dry Eye Symptoms through Reduction of Cornea Epithelial Cell Apoptosis and Maintenance of Conjunctival Goblet Cells in a Mouse Dry Eye Model", Journal of Food and Nutrition Research, 2017, vol. 5, No. 5, pp. 320-330.

* cited by examiner

*Primary Examiner* — Jennifer E Graser
(74) *Attorney, Agent, or Firm* — Birch, Stewart, Kolasch & Birch, LLP

(57) ABSTRACT

The present invention provides a method for preventing, postponing or treating ocular diseases, including changes in the anterior/posterior chamber volume, vitreous humour, and/or retinal detachment. The method comprises administering to a subject an effective amount of *Cordyceps cicadae* mycelium active substances. A method for preparing *Cordyceps cicadae* mycelium active substances comprises following steps: (a) culturing a *Cordyceps cicadae* mycelium on a plate medium between 15-35° C. for 5-14 days; (b) inoculating the *Cordyceps cicadae* mycelium of step (a) into a flask and culturing the mycelium between 15-35° C. and pH 2-8 for 3-7 days; and (c) inoculating the *Cordyceps cicadae* mycelium of step (b) into a fermenter tank and culturing the mycelium by stirring between 15-35° C. and pH 2-8 for 3-5 days, so as to obtain a *Cordyceps cicadae* mycelium fermentation liquid containing the *Cordyceps cicadae* mycelium active substances.

11 Claims, 2 Drawing Sheets

METHOD FOR PREVENTING, POSTPONING OR TREATING CHANGES IN THE ANTERIOR/POSTERIOR CHAMBER VOLUME, VITREOUS HUMOUR, AND/OR RETINAL DETACHMENT

BACKGROUND

Technical Field

The present invention relates to a method for preventing, postponing or treating steroid-induced ocular diseases, and in particular relates to a method for preventing, postponing or treating changes in the anterior/posterior chamber volume, vitreous humour, and/or retinal detachment.

Description of Related Art

*Cordyceps cicadae* (*C. cicadae*)

Description and Distribution

*Cordyceps cicadae*, also known as tǔ chán huā, chóng hu ā, chán cǎo, hú chán, chán jùn, chán yǒng cǎo, jīn chán hu ā, chán róng and cán róng, is a phylum of Ascomycotina, order of Claricipiyales, family of Clavicipitaceae and genus of *Cordyceps* fungi. *Cordyceps* species are insect-fungus complexes that strictly parasitize on the larva of *Cicada flammate, Platypleura kaempferi, Crytotympana pustulata, Platylomia pieli*, and many more. After parasitizing, the genus *Cordyceps* forms a flower bud-shaped stroma at the front end of the larva or on the head of the cicada, thus bearing the name chán huā (literally "cicada flower"). *C. cicadae, C. sobolifera* and *C. cicadicola* are the most common types of *Cordyceps* and are classified based on the hosts in which they reside. The genus is mainly distributed in subtropical and tropical regions south of the Yangtze River, i.e. Fujian, Zhejiang, Sichuan, Yunnan and Jiangsu in China. Fruit bodies of wild *C. cicadae* are also found in certain mountain regions in Taiwan.

The sexual stage of *Paecilomyces cicadae* is called dà chán cǎo (*C. cicadae*), also known as dú jiǎo lóng. It bears a brown, rod-shaped or horn-shaped solitary stroma or stromal clump, which sticks out from the head of the host. The most widely distributed species, however, is *Paecilomyces cicadae* (chán huā); *C. cicadae* (dà chán cǎo) remains scarce.

1. Steroids and their Use in Ophthalmology

Steroids can exert powerful anti-inflammatory and immune regulatory effects and are highly valuable in treating inflammatory diseases such as vasculitis, asthma, allergic diseases, chronic eczema, anaphylaxis, chronic obstructive pulmonary disease, autoimmune diseases (such as lupus erythematosus, dermatomyositis, polymyositis, glomerulonephritis, inflammatory arthritis and scleroderma), cerebral edema, certain types of inflammatory neuropathy and cancers (such as lymphoma). Common types of steroids include oxymetholone, testosterone undecanoate, oxandrolone, dehydromethyltestosterone, mepitiostane, stanozolol and the like. There are many types of steroid-containing preparations, which can be administered by injection, orally, nasally or topically.

Ophthalmic steroids are corticosteroids derived from adrenal glucocorticoids. Adrenal glucocorticoids, which commonly include cortisol and corticosterone, are secreted by the adrenal cortex and are normally present in the blood at a stable concentration level. As the body experiences greater external stress, more adrenal glucocorticoids are secreted into the blood (the reason for which they are also named "stress hormones"). Such increase of the secretion of adrenal glucocorticoids helps combat stress levels by reinforcing various physiological responses, including countering inflammation, maintaining blood pressure levels, raising blood sugar levels, absorbing calcium, secreting gastric acid and regulating the metabolism of proteins, fat, carbohydrates, electrolytes and water.

Steroids are used to treat ocular diseases mainly for the ability of corticosteroids to suppress inflammatory immune responses that occur in the body under various circumstances, as well as to alleviate a variety of inflammation-associated symptoms and sequelae. Corticosteroids are well-suited for patients present with anterior chamber inflammation or ocular autoimmune diseases, or those having received a corneal transplant. Ophthalmic steroids are typically ranked in the following order in terms of anti-inflammatory effects: betamethasone≥dexamethasone>>triamcinolone>prednisolone>>hydrocortisone.

2. Betamethasone

The steroids used in the present invention are Betamethasone, a type of corticosteroids approved for medical use in 1961 in the United States. Betamethasone is useful in treating a wide range of diseases, including rheumatic diseases such as rheumatoid arthritis and systemic lupus erythematosus, skin diseases such as dermatitis and psoriasis, and allergic diseases such as asthma and angioedema. It can also be used to stimulate lung development in preterm infants, as well as treat Crohn's disease, leukemia and, when used in conjunction with fludrocortisone, adrenal insufficiency. Betamethasone can be administered orally, by intramuscular injection or topically in the form of ointments. Included in the WHO Model List of Essential Medicines, Betamethasone ointments are among the most effective and safest drugs essential to public health systems and can be used as a generic drug.

Steroid-Induced Side Effects

Steroid-induced side effects are directly associated with dose and duration of use, and are more likely to occur when the drug is used for a long period of time or at high doses. Long-term use of steroids may result in adrenal insufficiency. On the other hand, steroid overdose may result in hypothalamic-pituitary-adrenocortical (HPA) axis abnormalities, which cause the adrenal cortex to stop functioning and eventually shrivel, and render the body dependent on steroids. Severe side effects include cardiovascular disorders, liver failure, diabetes, skin disorders, emotional instability, gastrointestinal disorders, increased risk for infections, muscular weakness, change of menstrual cycle, reduced reproductive functions in males and severe allergies.

Steroid-induced side effects may inhibit cellular immune functions in the eye and worsen the microbial infections that are originally present. Thus, steroid eye drops are typically used in conjunction with antibiotics. In addition, steroid eye drops may inhibit healing of corneal epithelial wounds and, if used over a long period of time, result in other ocular diseases such as elevated intraocular pressure and cataract.

In view of the above, reducing steroid-induced side effects that may occur in the body has become an issue at stake.

SUMMARY

According to one embodiment of the present invention, a method is provided for preventing, postponing or treating changes in the anterior/posterior chamber volume, vitreous humour, and/or retinal detachment, comprising administering to a subject an effective amount of *Cordyceps cicadae* mycelium active substances. A method for preparing *C. cicadae* mycelium active substances comprises following steps:

(a) culturing a *C. cicadae* mycelium on a plate medium between 15-35° C. for 5-14 days; (b) inoculating the *C. cicadae* mycelium of step (a) into a flask and culturing the mycelium between 15-35° C. and pH 2-8 for 3-7 days; and (c) inoculating the *C. cicadae* mycelium of step (b) to a fermenter tank and culturing the mycelium by stirring between 15-35° C. and pH 2-8 for 3-5 days, so as to obtain a *C. cicadae* mycelium fermentation liquid containing *C. cicadae* mycelium active substances.

In one embodiment, the method for preparing *C. cicadae* mycelium active substances further includes step (d): freeze-drying the *C. cicadae* mycelium fermentation liquid and grinding the freeze-dried product, so as to obtain a *C. cicadae* mycelium powder containing *C. cicadae* mycelium active substances.

In one embodiment, the method for preparing *C. cicadae* mycelium active substances further includes step (e): extracting the *C. cicadae* mycelium powder with a solvent, so as to obtain a *C. cicadae* mycelium fluid extract containing *C. cicadae* mycelium active substances.

In one embodiment, the method for preparing *C. cicadae* mycelium active substances further includes step (f): drying the *C. cicadae* mycelium fluid extract, so as to obtain *C. cicadae* mycelium active substances.

In one embodiment, the solvent of step (e) is selected from water or alcohol.

In one embodiment, the culturing of step (b) is shake flask cultivation, and a shaking speed is between 10-250 rpm.

In one embodiment, a gas is further fed into the fermenter tank of step (c), and the gas fed comprises air, oxygen, carbon dioxide, helium or a combination thereof. Pressure of the fermenter tank is 0.5-1.0 kg/cm$^2$, and a gas flow rate is 0.01-1.5 VVM.

In one embodiment, the *Cordyceps cicadae* mycelium active substances are included in a composition.

In one embodiment, the composition is a pharmaceutical composition which further comprises a pharmaceutically acceptable carrier, excipient, diluent or adjuvant.

In one embodiment, the *Cordyceps cicadae* mycelium active substances are a food additive.

In one embodiment, the *Cordyceps cicadae* mycelium active substances are administered in form of oral drugs, drops or suppositories.

For the purpose of further illustrating the above and other aspects of the present invention, several exemplary embodiments will be described with reference to the accompanying drawings.

DETAILED DESCRIPTION

Figure 1:
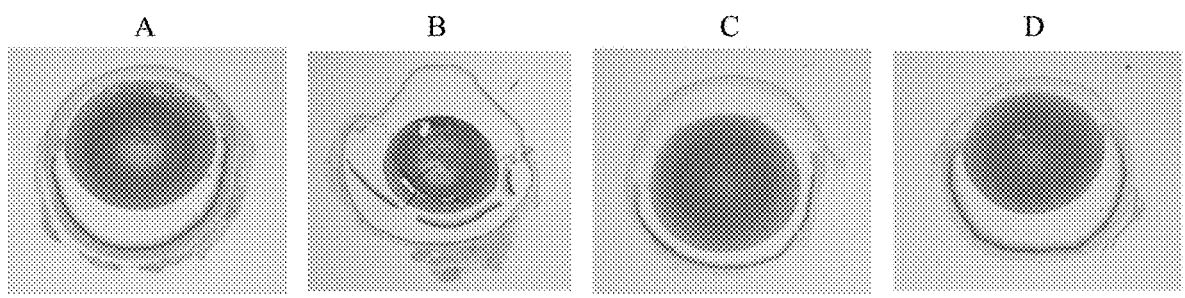
FIG. 1 shows the micrographs of H&E stained histological sections of eyes in rats from each group according to Example 2 of the present invention.

Method for Preparing *C. cicadae* Mycelium Active Substances

Source of *Cordyceps cicadae* Mycelium

*Cordyceps cicadae* (*C. cicadae*) mycelium of the present invention is obtained through the following steps: gathering a natural Taiwanese *C. cicadae* strain, separating its mycelium and storing the subculture on a plate medium. The gene sequence of the strain is confirmed as *C. cicadae* by Taiwan Food Industry Research and Development Institute. However, it should be noted that the *C. cicadae* mycelium active substances of the present invention are not limited to those derived from this genus.

Liquid Culture

*C. cicadae* mycelium is inoculated onto a plate medium between 15-35° C. (preferably at 25° C.) for 5 days to 2 weeks. Strains of the mycelium are then scraped from the plate and inoculated into a flask. The inoculated mycelium is incubated in the flask between 15-35° C. (preferably at 25° C.), pH 2-8 (preferably between pH 4-7, more preferably at pH 4.5), and at a shaking speed of 10-250 rpm for 3-7 days. The culture is further inoculated into a fermenter tank (similar to a culture flask), and is stirred between 10-150 rpm or air-lifted when the environment temperature is set between 15-35° C. (preferably at 25° C.), the tank pressure between 0.5-1.0 kg/cm$^2$ and the pH value between 2-8. Meanwhile, air (which can be replaced by air, oxygen, carbon dioxide, helium or a combination thereof, preferably air) is fed into the tank at a gas flow rate of 0.01-1.5 VVM. The resulting culture is incubated for 3-5 days and a *C. cicadae* mycelium fermentation liquid is obtained. The fermentation liquid comprises mycelium and supernatant. The above culture conditions are merely exemplary and can be adjusted according to the user's needs.

The recipe for the culture flask and the fermenter tank according to the present invention may include the following ingredients:

| Ingredient | Amount (weight %) |
|---|---|
| Mixed carbon and nitrogen sources | 0.01-5 |
| Animal or plant proteins and hydrolysates thereof | 0.01-2 |
| Yeast or malt extract (powder or cream) | 0.001-2 |
| Inorganic salts | 0.0001-0.05 |
| Carbohydrates | 0.01-10 |

Among the above ingredients, mixed carbon and nitrogen sources can be cereals (such as wheat flour) or legumes (such as soya bean powder, mung bean powder or *Glycine max* powder); inorganic salts can be magnesium sulfate, dipotassium phosphate, monopotassium phosphate, ferric sulfate and the like; and carbohydrates can be glucose, fructose, maltose, sucrose and the like. It should be noted that the recipe of the medium used in the present invention is not limited to the above ingredients or proportions and can be adjusted according to actual needs.

Drying of Fermentation Liquid

The fermentation liquid of the *C. cicadae* mycelium is further subject to a drying method so as to obtain freeze-dried powder or other dosage forms. The drying method includes but is not limited to spray drying, hot air drying, drum drying, freeze drying and the like.

Extraction—Water Extraction

The freeze-dried powder made from the fermentation liquid of the *C. cicadae* mycelium via a drying method can be dissolved in distilled water. The resulting solution can be heated between 90-121° C. for 20-120 minutes and dried after cooling, using vacuum concentration or one of the above drying methods, to obtain a water extract of the *C. cicadae* mycelium.

Extraction—Alcohol Extraction

The freeze-dried powder made from the fermentation liquid of the *C. cicadae* mycelium via a drying method can be dissolved in an alcohol solvent (such as 1-100% methanol or ethanol). The resulting solution can be extracted using a variety of methods, including, but not limited to dipping, stirring, agitation or ultrasonic extraction and dried using vacuum concentration or one of the above drying methods, for 20-120 minutes, to obtain an alcohol extract of the *C. cicadae* mycelium.

Each of the above fermentation liquid, freeze-dried powder, water extract and alcohol extract of the *C. cicadae* mycelium contains the *C. cicadae* mycelium active substances of the present invention. The preparation of *C. cicadae* mycelium active substances using the above methods, as well as the animal experiments conducted for evaluating the effects of the prepared substances, will be described in the following examples.

Example 1: Preparation of *C. cicadae* Mycelium Active Substances

Strains of *C. cicadae* mycelium: The *C. cicadae* strains used in this example are now publicly deposited in the Biosource Collection and Research Center (BCRC) of Taiwan Food Industry Research and Development Institute (BCRC number: MU30106), but the *C. cicadae* mycelium active substances of the present invention are not limited to the substances prepared from such strains.

Plate culture: The *C. cicadae* mycelium was inoculated onto a plate medium of Potato Dextrose Agar (PDA) and then incubated at 25° C. for 5 days.

Culture in a flask: *C. cicadae* mycelium strains were scraped from the plate and inoculated into a flask. The culture was grown at 120 rpm in a shaker incubator for 3 days at 25° C. and pH 4.5 using the following recipe:

Recipe for the Culture Medium:

| Ingredient | Amount (weight %) |
| --- | --- |
| Sucrose | 2.0 |
| Yeast extract | 0.5 |
| Soya bean powder | 1.0 |

Culture in a fermenter tank: The culture in the flask was further inoculated into a fermenter tank containing the above recipe, and was stirred between 10-150 rpm or air-lifted when the environment temperature was set at 25° C., the tank pressure between 0.5-1.0 kg/cm$^2$ and the pH value at 4.5. Meanwhile, air was fed into the tank at a gas flow rate of 0.5-1.0 VVM. The resulting culture was incubated for 3 days and a *C. cicadae* mycelium fermentation liquid was obtained. The fermentation liquid was then freeze-dried to obtain freeze-dried powder of *C. cicadae* mycelium.

Preparation of Extracts:

1. Water extraction: The freeze-dried powder of *C. cicadae* mycelium was dissolved in a 20-fold volume of distilled water. The solution was heated at 100° C. for 30 minutes, and freeze-dried after cooling to obtain a water extract of *C. cicadae* mycelium.

2. Alcohol extraction: The freeze-dried powder of *C. cicadae* mycelium was dissolved in a 20-fold volume of ethanol, and the solution was extracted in an ultrasonic bath for 1 hour. The extracted suspension was then centrifuged and the supernatant was vacuum-concentrated to obtain an alcohol extract of *C. cicadae* mycelium.

Results: 20 metric tons of *C. cicadae* mycelium fermentation liquid cultured in the fermenter tank were freeze-dried and processed into approximately 110 kg of freeze-dried powder (Yield: 0.55%). After ensuing extraction process, approximately 40 kg of water extract or 15 kg of alcohol extract were obtained. In the following example, animal experiments were conducted using water and alcohol extracts of *C. cicadae* mycelium.

Example 2: Animal Model of Steroid-Induced Ocular Diseases and Analysis of Stained Tissue Sections Establishment of a rat animal model with steroid-induced pathological changes in the eyes 1.1 Experimental Animals and Grouping SD male rats aged 7-8 weeks were used in this example. Free access to water and lab diet (LabDiet® 5001 Rodent diet, Purina Mills LLC, St. Louis, Mo., USA) were granted. All animals were housed under a controlled temperature of 22±2° C. and a 12-hour light/dark cycle.

The rats were divided into four groups of six: a blank control group, a negative control group, a water extract group and an alcohol extract group. All substances to be tested were administered into the right eye of the rats. All rats, except those in the blank control group, were given subconjunctival injection of betamethasone for 3 weeks to induce ocular diseases. The ocular diseases that were induced and observed include pathological changes in the anterior/posterior chamber volume and vitreous humour, lens degeneration and retinal detachment. It should be noted that the steroid drugs described herein are not limited to betamethasone.

1.2 Doses and Experimental Procedure

No *C. cicadae* mycelium active substances were given to the blank control group and the negative control group during the experiment. On the other hand, these substances were given orally at 50 mg/kg bw via a feeding tube to the water extract group and the alcohol extract group for 4 weeks.

At the end of the experiment, rats were anesthetized with $CO_2$ to collect blood samples from the abdominal aorta and sacrificed by bloodletting. Right eyeballs were collected and analyzed by macroscopic observation and histopathological examination.

Examination of Damage Severity in Various Parts of the Eye 2.1 Examination of Stained Tissue Sections Rats were anesthetized with $CO_2$ and blood sample was collected from the abdominal aorta by bloodletting. Right eyeballs were then collected and immersed in Davidson's Fluid (DF). After fixation for 48 hours in the fixative, the eyeballs were then placed into 10% neutral buffered formalin to be fixated for 1 week. Paraffin sections of the fixated tissue were subsequently prepared for histopathological examination. The fixated tissue was further made into paraffin-embedded tissue blocks using a paraffin embedder (Histoembedder, Leica, German) and then cut into 5-μm sections using a microtome (Leica, RM-2145, German). The sections were stained with H&E stain and mounted in gum arabic using an autostainer (Sakura model, DRS—60A). The mounted sections were examined by optical microscopy (BX51, Olympus, Tokyo, Japan) for observing histopathological changes, including changes in the anterior/posterior chamber volume and vitreous humour, lens degeneration and retinal detachment level. The results of examination are shown in FIGS. 1-4 in which Group A is the blank control group, Group B is the negative control group, Group C is the water extract group and Group D is the alcohol extract group.

FIG. 1 shows the micrographs of H&E stained histological sections of eyes in rats (20×), in which Group B exhibits retinal detachment and moderate changes in the anterior/posterior chamber volume along with changes in vitreous humour while Groups A, C and D exhibit no visible histopathological changes in the retina and anterior/posterior chamber volume.

Figure 2:
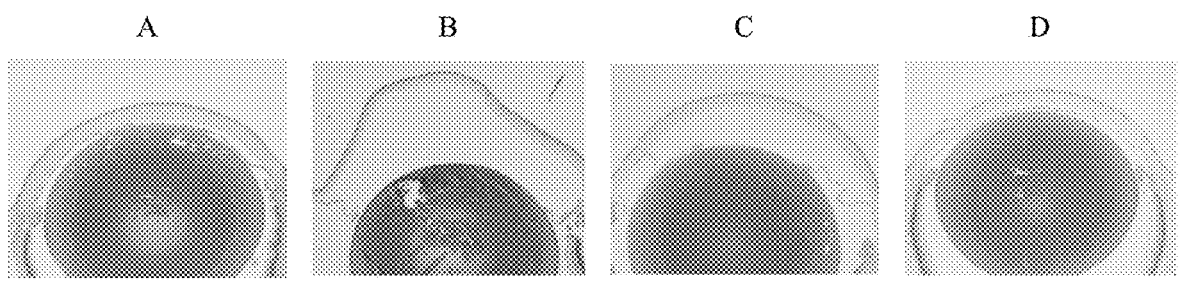
FIG. 2 shows higher magnification micrographs of H&E stained histological sections of eyes in rats from each group according to Example 2 of the present invention.

FIG. 2 shows the higher magnification micrographs of H&E stained sections histological sections of eyes (40×), in which Group B exhibits moderate changes in the anterior/posterior chamber volume along with changes in vitreous humour, while Groups A, C and D exhibit no visible histopathological changes in the anterior/posterior chamber volume.

Figure 3:
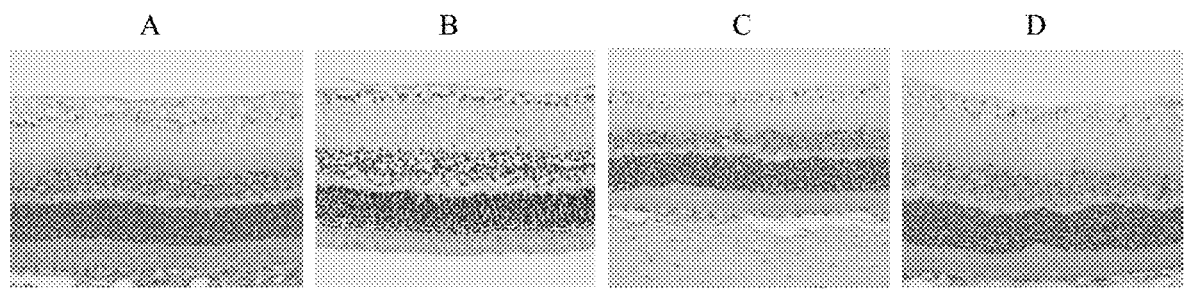
FIG. 3 shows higher magnification micrographs of H&E stained histological sections of retinas in rats of each group according to Example 2 of the present invention.

FIG. 3 shows higher magnification micrographs of H&E stained histological sections of retinal tissue (400×), in which Group B exhibits reduced retinal thickness, abnormal retinal ganglion cell morphology and marked empty spaces between the nuclei of inner nuclear layer, while Groups A, C and D exhibit no visible histopathological changes in retinal tissue.

Figure 4:
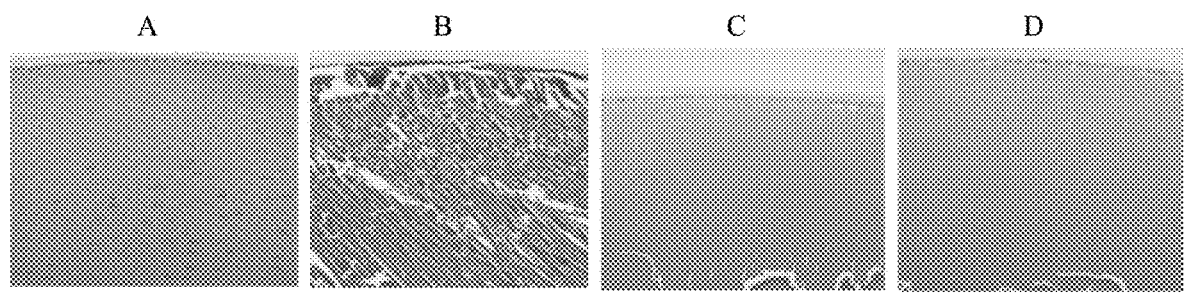
FIG. 4 shows higher magnification micrographs of H&E stained histological sections of lenses in rats of each group according to Example 2 of the present invention.

FIG. 4 shows higher magnification micrographs of H&E stained histological sections of lens tissue (400×), in which. Group B exhibits clefts in the lens while Groups A, C and D exhibit no visible histopathological changes in lens tissue.

2.2 Histopathological Examination of Eyeballs

The damage severity of induced ocular diseases are classified into 5 grades: Grade 1=Minimal (<1%); Grade 2=Mild (<1-25%); Grade 3=Moderate (26-50%); Grade 4=Moderate/Severe (51-75%); and Grade 5=Severe/High (76-100%). Based on the results from the histopathological examination on each part of the eyeball tissue, a table of pathological scores is made as follows, wherein the eyeball tissue includes anterior/posterior chamber, vitreous humour, cornea, choroid, sclera, retina and lens.

a score of 4; the change in the retina is minimal, resulting in a score of 1; and the change in the lens is minimal, resulting in a score of 1. On the other hand, the water extract group and the alcohol extract group exhibit no histopathological changes in any part of the eyeball tissue, and variations between these groups and the negative control group are statistically significant.

The above results show that *C. cicadae* mycelium active substances can prevent, postpone or treat ocular diseases, including changes in the anterior/posterior chamber volume and vitreous humour and retinal detachment, particularly histopathological changes induced by steroids.

In Example 2, *C. cicadae* mycelium active substances were administered orally to rats. As such, *C. cicadae* mycelium active substances may be used as medications, dietary supplements or food additives. However, routes of administration for the *C. cicadae* mycelium active substances of the present invention are not limited to oral drugs but include injection, drops, suppositories and the like.

In summary, as disclosed in the embodiments of the present invention, the *C. cicadae* mycelium fermentation liquid, *C. cicadae* mycelium freeze-dried powder, *C. cicadae* mycelium water extract and alcohol extract and a pharmaceutical composition manufactured therefrom, all of which contain *C. cicadae* mycelium active substances, are useful in preventing, postponing or treating ocular diseases, including changes in the anterior/posterior chamber volume and vitreous humour and retinal detachment. Accordingly, the fermentation liquid, freeze-dried powder, water extract and alcohol extract containing *C. cicadae* mycelium active substances can be processed, using food production methods known in the art, into dietary supplements for preventing or postponing said ocular diseases.

What is claimed is:

1. A method for preventing, postponing or treating steroid-induced ocular changes in the anterior/posterior chamber volume, vitreous humour, and/or retinal detachment, comprising administering to a subject an effective amount of *Cordyceps cicadae* mycelium active substances, wherein the administration is drops to the eyes or oral administration, wherein a method for preparing the *Cordyceps cicadae* mycelium active substances comprises following steps:

|  | Anterior/posterior chamber | Vitreous humour | Cornea | Choroid and sclera | Retina | Lens |
|---|---|---|---|---|---|---|
| Blank control group A | 0 ± 0 | 0 ± 0 | 0 ± 0 | 0 ± 0 | 0 ± 0 | 0 ± 0 |
| Negative control group B | 3.2 ± 0.8 | 3.5 ± 0.5 | 3.5 ± 0.8 | 4.5 ± 1.2 | 1.7 ± 0.8 | 1.3 ± 1.0 |
| Water extract group C | 0.7 ± 1.0** | 0 ± 0** | 0 ± 0** | 0 ± 0** | 0 ± 0** | 0 ± 0** |
| Alcohol extract group D | 0 ± 0** | 0 ± 0** | 0 ± 0** | 0 ± 0** | 0 ± 0** | 0 ± 0** |

1. Results are shown as Mean ± SD (n = 6) after calculation.
2. The asterisks (**) indicate that variations between the blank control group and the negative control group are statistically significant with p < 0.01. Variations within groups are compared using one-way ANOVA, while variations between groups are compared using Duncan.

As shown in the above table of pathological scores, the blank control group exhibits no histopathological changes in any part of the eyeball tissue. The negative blank group exhibits histopathological changes in each part of the eyeball tissue, wherein the change in the anterior/posterior chamber is moderate, resulting in a score of 3; the change in the vitreous humour is moderate, resulting in a score of 3; the change in the cornea is moderate, resulting in a score of 3; the changes in the choroid and sclera are severe, resulting in (a) culturing a *Cordyceps cicadae* mycelium on a plate medium between 15-35° C. for 5-14 days;

(b) inoculating the *Cordyceps cicadae* mycelium of step (a) into a flask and culturing the mycelium between 15-35° C. and pH 2-8 for 3-7 days; and (c) inoculating the *Cordyceps cicadae* mycelium of step (b) into a fermenter tank and culturing the mycelium by stirring between 15-35° C. and pH 2-8 for 3-5 days, so as to obtain a *Cordyceps cicadae* mycelium fermentation liquid containing the *Cordyceps cicadae* mycelium active substances.

2. The method of claim 1, wherein the method for preparing the *Cordyceps cicadae* mycelium active substances further includes step (d): freeze-drying the *Cordyceps cicadae* mycelium fermentation liquid and grinding the freeze-dried product, so as to obtain a *Cordyceps cicadae* mycelium powder containing the *Cordyceps cicadae* mycelium active substances.

3. The method of claim 2, wherein the method for preparing the *Cordyceps cicadae* mycelium active substances further includes step (e): extracting the *Cordyceps cicadae* mycelium powder with a solvent, so as to obtain a *Cordyceps cicadae* mycelium fluid extract containing the *Cordyceps cicadae* mycelium active substances.

4. The method of claim 3, wherein the method for preparing the *Cordyceps cicadae* mycelium active substances further includes step (f): drying the *Cordyceps cicadae* mycelium fluid extract, so as to obtain the *Cordyceps cicadae* mycelium active substances.

5. The method of claim 4, wherein the solvent of step (e) is selected from water or alcohol.

6. The method of claim 1, wherein the culturing of step (b) is shake flask cultivation, and a shaking speed is between 10-250 rpm.

7. The method of claim 1, wherein a gas is further fed into the fermenter tank of step (c), and the gas fed comprises air, oxygen, carbon dioxide, helium or a combination thereof; pressure of the fermenter tank is 0.5-1.0 $kg/cm^2$, and a gas flow rate is 0.01-1.5 VVM.

8. The method of claim 1, wherein the *Cordyceps cicadae* mycelium active substances are included in a composition.

9. The method of claim 8, wherein the composition is a pharmaceutical composition, which further comprises a pharmaceutically acceptable carrier, excipient, diluent or adjuvant.

10. The method of claim 1, wherein the *Cordyceps cicadae* mycelium active substances are food additives.

11. The method of claim 1, wherein the *Cordyceps cicadae* mycelium active substances are administered in form of oral drugs, drops or suppositories.

* * * * *